United States Patent [19]
Lemelson et al.

[11] Patent Number: 5,836,905
[45] Date of Patent: Nov. 17, 1998

[54] APPARATUS AND METHODS FOR GENE THERAPY

[76] Inventors: Jerome H. Lemelson, Suite 286, Unit 802, 930 Tahoe Blvd., Incline Village, Nev. 89451; J. Kevin Parker, 551 Green Bay Rd., Highland Park, Ill. 60035

[21] Appl. No.: 775,047

[22] Filed: Dec. 27, 1996

Related U.S. Application Data

[63] Continuation of Ser. No. 262,581, Jun. 20, 1994, abandoned.

[51] Int. Cl.⁶ ........................................................ A61N 1/30
[52] U.S. Cl. ............................... 604/21; 604/102; 606/15; 607/116
[58] Field of Search .................................. 604/15, 16, 20, 604/21, 41, 51–53, 102, 104, 163, 171, 264; 607/116, 89; 935/52–54, 85; 600/115, 373; 606/15, 16

[56] References Cited

U.S. PATENT DOCUMENTS

| | | | |
|---|---|---|---|
| 5,120,657 | 6/1992 | McCabe et al. | 435/287 |
| 5,486,170 | 1/1996 | Winston et al. | 606/16 |
| 5,507,724 | 4/1996 | Hofmann et al. | 604/53 |

*Primary Examiner*—Corrine M. McDermott
*Assistant Examiner*—A. T. Nguyen

[57] ABSTRACT

A method and apparatus are disclosed for the in vivo transfer of therapeutic genes to internal body sites. An operating head of a catheter or endoscope contains a particle bombardment device for accelerating DNA-coated particles into a target tissue. With either endoscopy or arterial catheterization, the operating head may be guided to diseased or deficient organs, or other lesions, and deliver the gene coated particles in a targeted manner. In one embodiment, a double balloon catheter is employed to isolate an intravasular space containing the lesion to be treated, with the space being cleared of blood and filled with gas before operation of the particle bombardment device. The method and apparatus may also be employed to deliver other therapeutic agents to intracellular targets.

17 Claims, 3 Drawing Sheets

APPARATUS AND METHODS FOR GENE THERAPY

This application is a continuation of Ser. No. 08/262,581, filed Jun. 20, 1994, now abandoned.

BACKGROUND AND SUMMARY OF THE INVENTION

It is the goal of gene therapy to treat inherited and acquired disease through the transfer of genes to the somatic cells of a patient so that a therapeutic effect is obtained from the expression of the transferred genes. The transferred genes or genetic material may act as replacements for defective genes, as in the case of inherited disease, or may produce gene products which attenuate or reverse a disease process such as neoplasia, infection, or other disease.

Two different strategies have evolved for introducing recombinant genes into somatic cells. One such strategy, the ex vivo approach, involves the removal and isolation of cells of a defined type from a patient, introduction of the recombinant gene into the cells, and replacement of the cells back into the body. The ex vivo approach has been particularly successful in introducing genes into lymphocytes. It cannot be used, however, unless the cells to be genetically modified are of a type which is amenable to culture outside the body and which can then be reimplanted back into the appropriate tissue. The other strategy for somatic gene transfer is the direct approach where genes are introduced into the appropriate cell type in vivo without the need for removing and culturing cells from the patient. Direct gene transfer may be especially appropriate in treating acquired disease whose pathology is anatomically localized such as malignancies or inflammatory processes.

A number of methods have been developed for transferring foreign DNA into cells. Some methods, such as microinjection, electroporation, and particle bombardment, rely on a physical process to deliver the DNA into the cell. Other methods employ chemical agents, such as calcium phosphate, to produce changes in the cell membrane in order to allow the diffusion of DNA into the cytoplasm. Foreign DNA can also be introduced into cells via carriers such as liposome-DNA complexes and recombinant viral vectors. Some of these methods, such as calcium phosphate transfection, are for practical reasons not suitable for in vivo gene transfer. Others, such as liposomal and viral transfection, while allowing the in vivo transfer of DNA, are not able to precisely target a tissue.

Gene transfer by particle bombardment presents several advantages over the other methods mentioned above. In this technique, microscopic particles coated with the gene to be transferred are accelerated by a shock wave in a gaseous medium so that the particles are able to penetrate cells and deliver the DNA thereto. The shock wave may be produced by a variety of means including high-voltage electrical discharge (See McCabe et al., *Bio/Technology* 6, 923 (1992); U.S. Pat. No. 5,149,655) or helium pressure discharge (See Williams et al., *Proc Natl Acad Sci USA* 88, 2726(1991)).

Particle bombardment is particularly suitable for in vivo gene transfer because the discharge of particles may be targeted at select or specific tissue so that surrounding cells can be left unaffected. Furthermore, since the particles are physically forced into the cell, this method overcomes the problems associated with the cell membranes of certain cell types which render those cells resistant to transfection with viral or liposomal carriers. In vivo gene transfer using particle bombardment requires that the target tissue be physically exposed. This means that the in vivo use of the technique for internal organs and tissues has heretofore required surgical procedures to expose the target site.

The present invention is a method and apparatus for effecting in vivo gene transfer to internal body sites such as within blood vessels, organs, the digestive tract, and body cavities. In accordance with the invention, a particle bombardment device attached to a catheter, endoscope, or hollow needle such as a hypodermic needle is introduced into an internal body site adjacent the target area. Prior to particle bombardment, fluid within the blood vessel or body cavity may be displaced by an injected gas which serves to both better expose the targeted tissue site and minimize frictional drag on the accelerated particles. Particles made of a chemically inert substance such as gold or diamond (either synthetic or natural) and coated with recombinant DNA are then accelerated into the target tissue by the bombardment device so that the accelerated particles penetrate the target cells and deliver genes thereto. Besides recombinant DNA, the particles may also be coated with other substances which it is desired to deliver intracellularly such as antibodies, RNA, proteins, viral particles, hormones, or antibiotics. For example, viral antigens delivered intracellularly to certain cells may cause the cells to express the antigens on their surfaces and induce an immune response to the antigen. Monoclonal antibodies may also be delivered to the interior of cells by particle bombardment where the antibodies bind to specific intracellular targets.

One embodiment of the apparatus is a gene therapy catheter which comprises an elongated hollow flexible tubular member attached to an operating head adapted to be inserted within a blood vessel. The operating head contains a particle bombardment device disposed therein for discharging DNA-coated particles or the like out through a discharge port so that the particles impinge on a target tissue and deliver DNA intracellularly thereto. The catheter may also have proximal and distal balloons girthing the tubular member on either side of the operating head with a balloon inflation line running through the catheter so as to provide inflation pressure to the balloons. Inflation of the proximal and distal balloons against the walls of an artery in which the catheter is inserted serves to isolate a space therebetween through which space DNA-coated particles may be discharged from the operating head or the side wall of the catheter toward a target tissue. The catheter may also include suction and gas injection ports communicating with suction and gas injection lines running through the catheter which enable body fluids in the space isolated by the proximal and distal balloons to be displaced by gas. In order to seal the discharge port from body fluids until the fluids are removed from the space isolated by the proximal and distal balloons, the operating head may be constructed of telescoping proximal and distal sections which act to seal and unseal the discharge port in accordance with the operation of a hydraulic cylinder and piston.

Another embodiment of the invention is an endoscope, laparascope, catheter, hollow needle, or the like adapted to be inserted within a body cavity comprising an elongated hollow tubular member attached to an operating head which contains a particle bombardment device similar to that described above. The tubular member also contains an incoherent fiber optic bundle for transmitting light out through the operating head in order to illuminate the region in which the operating head is located, and a coherent fiber optic bundle for transmitting visual images of the illuminated region to an eyepiece or other visual monitor so as to enable the operating head to be guided to the target tissue.

It is therefore a primary object of the present invention to provide an apparatus and method for enabling the in vivo transfer of genetic or other therapeutic material to internal body tissues in a targeted manner without the need for surgical procedures.

It is a further object of the invention to provide an apparatus and method for the treatment of vascular ailments such as atherosclerotic blood vessel disease using gene therapy.

It is a further object of the invention to provide an apparatus and method for the treatment of diseases affecting the digestive tract and internal body organs using gene therapy.

Other objects, features, and advantages of the invention will become evident in light of the following detailed description considered in conjunction with the referenced drawings of a preferred exemplary embodiment according to the present invention.

DETAILED DESCRIPTION OF THE INVENTION

Figure 1:
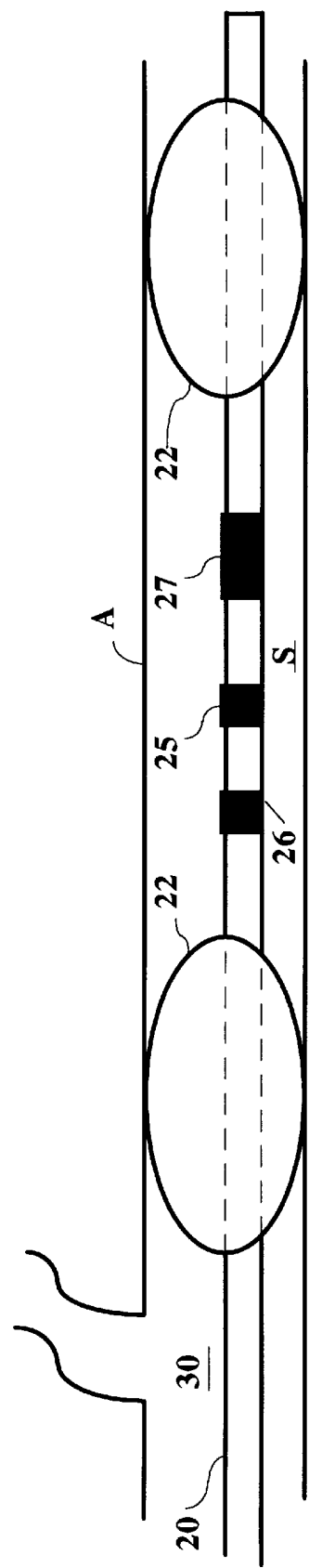
FIG. 1 depicts a double balloon gene therapy catheter inserted into an artery and with the balloons inflated to isolate the target site.

FIG. 1 shows a gene therapy catheter 20 in accordance with the present invention which has been inserted into an artery A. The operating head 21 of the catheter is guided by visual, radiographic or other means to the target site within the artery. The catheter has proximal and distal balloons 22 which, when inflated, isolate a space S therebetween which contains the region of the artery where it is desired to transfer genetic material by particle bombardment. For the particles to reach their target in the arterial wall, in one embodiment, the space between the balloons 22 should be cleared of liquid and replaced with a gas. A port 25 allows suctioning of the blood residing within the space isolated by balloons 25 while simultaneously injecting air or other gas through port 26. In this way, a suitable environment is provided for gene particle bombardment out through port 27.

Figure 2:
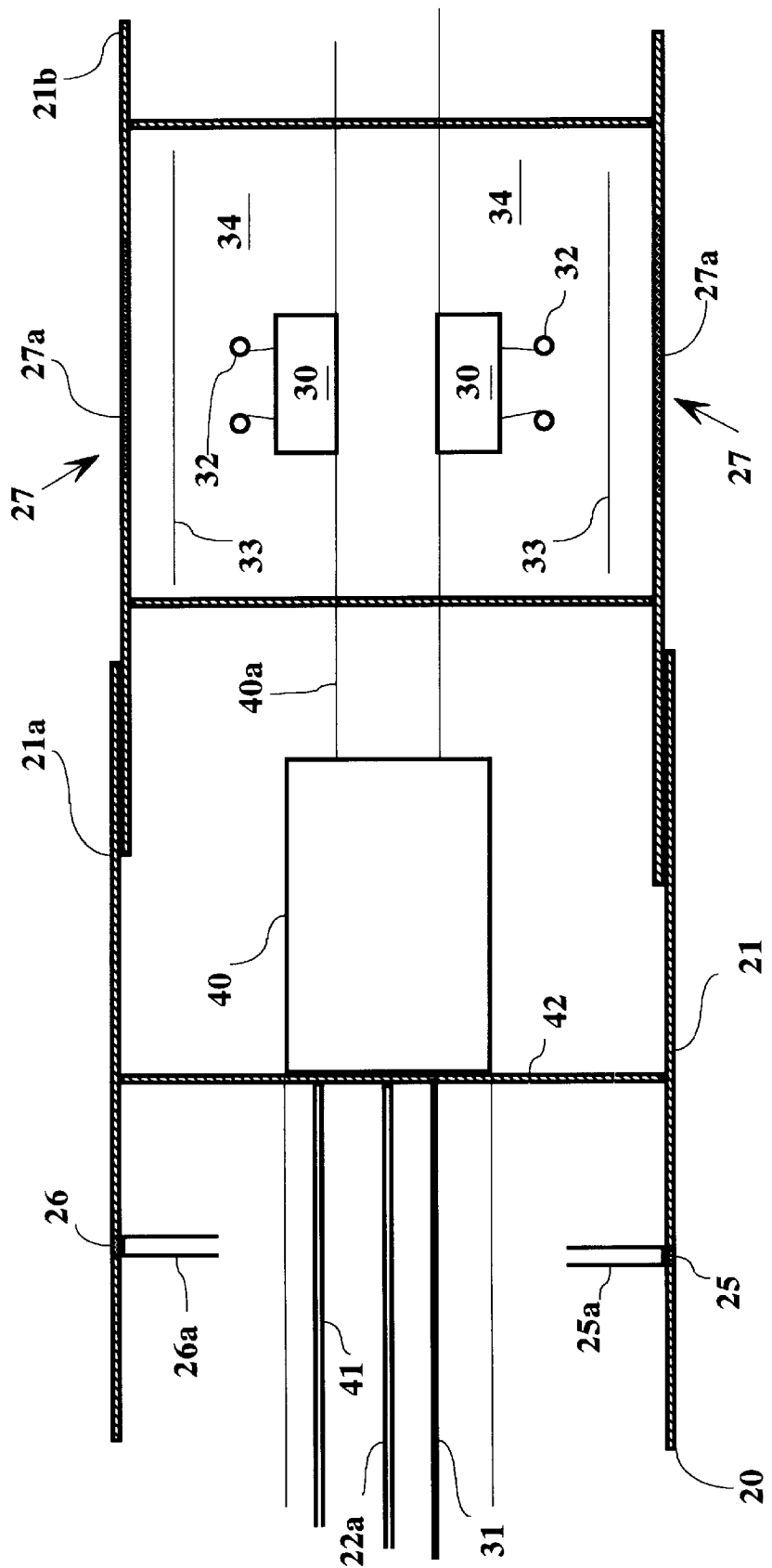
FIG. 2 shows in partial cross-section the catheter of FIG. 1 in more detail.

FIG. 2 shows one form of the operating head 21 of a catheter 20, which head is located between balloons 22, in more detail. After the catheter is positioned within the artery and balloons 22 are inflated, blood is suctioned into suction line 25a through suction port 25 while simultaneously filling the intravascular space with gas from injection line 26a through injection port 26. Suction port 25 and injection port 26 have disposed therein one-way check valves which keep the ports closed when lines 25a and 26a are supplied with negative and positive pressures, respectively. Two particle bombardment devices 30 are shown which cause acceleration of DNA-coated particles radially outward through ports 27 and thence into the arterial walls. A spark discharge between electrodes 32 is employed to vaporize a water droplet deposited therebetween from a nozzle (not shown) which then creates a shock wave in discharge chamber 34 with the operation of the electrodes and water nozzle controlled via a control cable 31. The shock wave propels a carrier sheet 33 suspended within chamber 34 out toward port 27. The carrier sheet 33 has precipitated thereon DNA-coated gold or diamond particles, and its function is to transfer the momentum of the shock wave to the particles. Disposed within port 27 is a mesh screen which serves to retain the carrier sheet while allowing the accelerated particles to proceed to the target tissue. The force of the shock wave and the resulting acceleration imparted to the particles may be varied by adjusting the voltage applied to the electrodes. In order to prevent blood from entering the discharge chamber 34 while the catheter 20 is being guided to its target location, the operating head of the catheter is constructed of two telescoping sections 21a and 21b. In this position, ports 27 are sealed by the walls of section 21a. After inflation of the balloons 22 and instillation of gas into the intravascular space, a hydraulic cylinder 40 and piston 40a controlled by hydraulic line 41 forces section 21b outward so as to expose the ports 27. Inflation line 22a runs coaxially through cylinder 40 and piston 40a in order to reach the distal section of the catheter. Distal section 21b is normally maintained seated within proximal section 21a against retaining wall 42 by the action of a spring mounted between the two sections or by the maintenance of negative pressure within cylinder 40.

Figure 3:
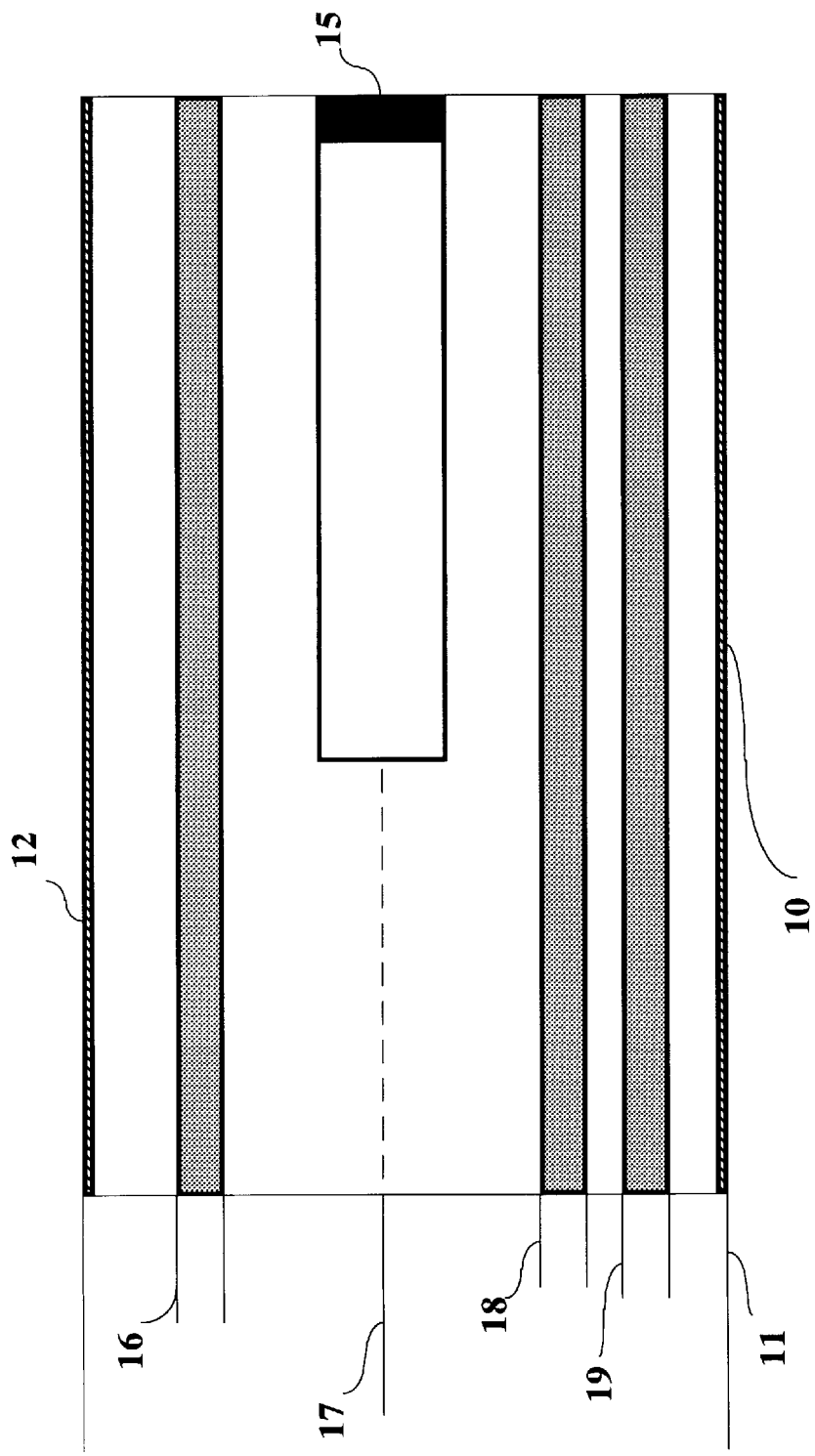
FIG. 3 shows schematically the operating head of a gene therapy endoscope.

FIG. 3 depicts schematically the components of a gene therapy endoscope 10 in accordance with the present invention. Such an endoscope may take the form of any a number of instruments designed to access specific body regions and thus may be either a bronchoscope, arthroscope, cystoscope, proctoscope, gastroscope, laparoscope, or similar device. The endoscope 10 comprises a relatively flexible section 11 attached to an operating head 12. Operating head 12 contains a gene particle bombardment device 15 which is similar to the device 30 described above with reference to FIG. 2. Bombardment device 15 operates so as to discharge DNA-coated particles out the end of operating head 12 in accordance with a control and/or power signals conveyed by control cable 17. The head 12 may be angled with respect to the longitudinal axis of the body duct or other structure into which the head is inserted so that the particles are directed at the duct wall. The particles may be propelled from an opening in the sidewall of the head 12, behind the head, or from one or more openings axially aligned with the longitudinal axis or the head or its tubular support. Also contained within the endoscope are an incoherent optic fiber bundle 18 for carrying and emitting light conducted therethrough from an external light source to illuminate the body region being accessed by the endoscope, and a coherent optic fiber bundle 19 for transmitting visual images from the illuminated region to enable the operating head to be guided to the target tissue. A gas line 16 is also provided for insufflating a body region in order to displace body fluid or distend a body wall so as to facilitate visualization and access to the target tissue.

A primary application of a gene therapy catheter as described above is in the treatment of atherosclerotic disease of the blood vessels, especially when combined with other treatment modalities. One such example is the use of the gene therapy catheter 20 to deliver DNA to the arterial wall following percutaneous transluminal angioplasty (PCTA). PCTA uses a balloon catheter to compress or fracture atheroscerotic plaque in order to restore patency to a partially occluded artery. Restenosis of vessels following PCTA is a major clinical problem and has been found to occur in 30–40% of patients within six months after the procedure. The restenotic lesion has been found from histological studies to result from a reactive hyperplasia of smooth muscle cells together with deposition of extracellular matrix in the area of the atherosclerotic plaque fractured by the angioplasty procedure. By introducing recombinant genes which inhibit smooth muscle cell proliferation into the atherosclerotic lesion following PTCA, the problem of restenosis can be greatly ameliorated even if the genes are only transiently expressed. One approach which has been found to effectively prevent restenosis following PTCA is the extravascular introduction of antisense c-myb oligonucleotides. (See Simons et al., *Nature* 359, 67 (1992)). A gene therapy catheter in accordance with the present invention may thus be used to deliver intravascularly either antisense nucleotides or recombinant genes (which either manufacture such antisense oligonucleotides or other growth suppressive gene products) directly to smooth muscle cells. Such gene therapy as described above may also be employed without previous PTCA to atherosclerotic lesions which are not amenable to angioplasty because of location (e.g., cerebral arteries) or nature of the lesion. In that case, the object of the treatment is to either slow the progression, or cause the regression, of atherscerotic plaque, which, if left unchecked, tends to grow and progressively narrow the artery. Particle bombardment of the target tissue is particularly useful in this application as it allows for efficient penetration of the DNA-coated particles past the intimal endothelial layer and into the media of the artery containing the smooth muscle cells.

Another type of genetic material which may be transferred to vascular cells in the treatment of athersclerosis are genes encoding products with an antithrombotic effect. Thrombosis, or clotting, of vessels partially occluded by athersclerotic lesions is the primary cause of most myocardial infarctions. Thrombus formation is due to the actions of platelets and coagulation proteins in the blood. Endothelial cells, rather than being inert barriers between platelets, clotting factors, and the subendothelial tissues, are known to actively participate in the regulation of hemostasis by both influencing platelet activity and modulating the coagulation system. Endothelial cells secrete a prostaglandin, $PGI_2$ or prostacyclin, which is a powerful inhibitor of platelet aggregation and a potent vasodilator and also enzymatically degrade adenosine diphosphate (ADP) in the serum which is another platelet-aggregating agent. Genes encoding prostacyclin or ADP-degrading enzymes may thus be delivered to endothelial cells by the gene therapy catheter where they act to inhibit the aggregation of platelets into a hemostatic plug. Endothelial cells also express two cell-surface molecules with powerful anticoagulant effects, heparan sulfate and thrombomodulin. Heparan sulfate facliltates the action of serum antithrombin III in inactivating thrombin as well as coagulation factors IXa and Xa. Thrombomodulin, conjunction with thrombin, activates serum protein C which exerts an anticoagulant effect by proteolytically cleaving factors V and VIII. When extra copies of genes encoding these products are transferred to the endothelial cells of a targeted region via the gene therapy catheter and expressed, the chances of an acute occlusion due to thrombus formation are lessened.

The in vivo transfer of genes to the heart may also be performed via a catheter or the like. A catheter of the type shown in FIG. 1 may be advanced to the right heart chambers through any systemic vein. Access to the left ventricle is gained by passing the catheter through the aortic valve from brachial or femoral arteries. Once the operating head of the catheter is inserted within a heart chamber, discharge of DNA-coated particles transfers genetic material into the subendocardial tissues to produce a therapeutic effect. Such genetic material may include genes for encoding the $\beta_2$-adrenergic receptor. Increased expression of the $\beta_2$-adrenergic receptor by cardiac muscle cells is useful in the treatment of congestive heart failure by making the heart more responsive to the ionotropic and chronotropic effects of endogenous adrenaline as well as adrenaline-like drugs. (See Milano et al., *Science* 264, 582 (1994)). Other types of genetic material which may be introduced into the heart via catheter for therapeutic effect include genes encoding dystrophin in order to treat the cardiomyopathy associated with Duchenne muscular dystrophy, and genes for angiogenic growth factors which stimulate the development of collateral blood vessels to areas of ischemic mycardium in order to treat coronary artery disease.

A gene therapy endoscope such as that of FIG. 3 may be used to effect the targeted delivery of genes to a number of internal body sites and treat a number of pathological conditions. Solid tumors accessible by the endoscope may be treated by transferring genes encoding substances which stimulate a host immune response against the tumor cells such as interleukins and class I major histocompatibility complex (MHC) molecules as well as transferring genes encoding tumor suppressors such as p53 and p16. Centrilobular emphysema may be treated by passing a fiber optic bronchoscope into the respiratory bronchioles and discharging particles coated with genes encoding alpha-1-antitrypsin. The increased levels of alpha-1-antitrypsin serve to inhibit elastase and other enzymes which, by degrading elastin and other connective tissue components in the lung, are involved in the pathogenesis of emphysema. For the treatment of arthritis, genes may be arthroscopically transferred which encode proteins promoting cartilage regeneration to articular chondrocytes such as insulin-like growth factor (IGF-1), basic fibroblast growth factor (bFGF), and transforming growth factor-$\beta$ (TGF-$\beta$), as well as anti-inflammatory proteins.

The apparatus and methods of the present invention have been described above as using particle bombardment as the sole means for effecting gene transfer. Particle bombardment may also be used in conjunction with other gene transfer methods such as viral and liposomal transfection in accordance with the present invention. In such cases, the transducing virus or liposomal preparation is first applied to the target tissue and then followed by bombardment of the tissue with either coated or uncoated particles. The penetrating particles then produce pathways within the tissue which allow the virus or liposomes to penetrate more deeply into the target tissue and deliver the genes thereto. Select tissue adjacent the instrument's operating head may also be prepared to receive DNA-coated particles by mechanically, electrically, or otherwise operating on the surfaces of cells making up the tissue such as through the use laser, microwave, or other types of radiation emitted from the operating head.

Any of the embodiments of the invention described above may also be used to deliver material other than DNA to the interior of target cells for therapeutic effect. Gold or diamond particles may be coated with agents such as monoclonal antibodies, small peptides, proteins, or drugs which, when delivered intracellularly to target cells, act to either kill or beneficially affect the cells. For example, cancer cells may be bombarded with particles coated with enzymes or catalytic antibodies, where the enzyme or antibody catalyzes a lethal reaction inside the cell. In another example, monoclonal antibodies directed against oncoproteins are delivered to the cytoplasm of cancerous cells where the antibodies neutralize the activity of the oncoprotein and restore a normal growth pattern to the cells.

In other embodiments of the invention, a small quantity of explosive in the operating head of the catheter or endoscope is employed to accelerate the particle or particles of gold, diamond, or other material into the cells adjacent the head or opening through which the particles are propelled. The explosive may be a solid chemical, liquid, or gas ignited by a spark or laser beam. The gas or liquid may be flowed through a tube in the instrument to an open end thereof passing sparking electrodes. An exploding wire ignited by a high voltage or resistance heating means may also generate the shock or pressure wave. The particles coated with genetic material may be mixed with the explosive, bonded to the wire, or propelled through a small opening subjected to the fluid pressure of the explosion. A pulsed laser beam may be used to generate a shock wave or pressure pulse in a gas or liquid to directly act to propel the particles or may ignite an explosive (pellet, particles, liquid, or gas) in a chamber.

In another embodiment, a fine intense laser beam may be passed through and out the end of a light pipe at the end of the instrument and to form a small opening in one or more cell walls wherein a particle or particles forced to travel along or adjacent the beam by gas or liquid pressure or a shock or pressure wave may be caused to enter the cell.

Although the invention has been described in conjunction with the foregoing specific embodiment, many alternatives, variations, and modifications will be apparent to those of ordinary skill in the art. Those alternatives, variations, and modifications are intended to fall within the scope of the following appended claims.

What is claimed is:

1. A catheter for transferring medical material in vivo to a target tissue comprising:
   an elongated hollow flexible tubular member adapted to be inserted within a blood vessel;
   an operating head attached to said tubular member and containing a particle bombardment device disposed therein for discharging particles coated with medical material so that particles impinge in vivo on target tissue and deliver the medical material intracellularly thereto;
   a discharge port disposed on said operating head out through which are discharged said particles wherein said operating head further comprises telescoping proximal and distal sections which act to seal and unseal said discharge port;
   a hydraulic cylinder within said operating head for moving one of said telescoping sections with respect to the other so as to seal and unseal said discharge port;
   proximal and distal balloons girthing said tubular member supported adjacent said operating head; and
   a balloon inflation line running through said tubular member and communicating with said proximal and distal balloons so as to provide inflation pressure thereto wherein inflation of said proximal and distal balloons against the walls of an artery or other body duct in which said catheter is inserted serves to isolate a space therebetween into which coated particles may be discharged from said operating head toward a target tissue.

2. A catheter in accordance with claim 1 further comprising suction and gas injection lines and respective ports communicating with said suction and gas injection lines running through said tubular member which enable body fluids in the space isolated by said proximal and distal balloons to be displaced by gas.

3. A catheter in accordance with claim 1 wherein said particle bombardment device comprises:

a pair of electrodes for vaporizing a liquid droplet in a discharge chamber so as to create a shock wave therein;
a carrier sheet suspended within said discharge chamber and onto which are precipitated coated gold particles; and
a mesh screen within said discharge port for retaining said carrier sheet when the latter is propelled thereagainst by a shock wave while allowing the accelerated coated particles to proceed to the target tissue.

4. A catheter in accordance with claim 1 wherein said particle bombardment device comprises:
   a laser for vaporizing a liquid droplet in a discharge chamber so as to create a shock wave therein;
   a carrier sheet suspended within said discharge chamber and onto which are precipitated coated diamond particles; and
   a mesh screen within said discharge port for retaining said carrier sheet when the latter is propelled thereagainst by a shock wave while allowing the accelerated coated particles to proceed to the target tissue.

5. A catheter in accordance with claim 1 wherein said particle bombardment device comprises:
   an explosion generating means for creating a shock wave in a discharge chamber;
   a carrier sheet suspended within said discharge chamber and onto which are precipitated coated gold particles; and
   a mesh screen within said discharge port for retaining said carrier sheet when the latter is propelled thereagainst by a shock wave while allowing the accelerated coated particles to proceed to the target tissue.

6. A method for transferring genetic material to target cells lining a blood vessel comprising:
   advancing a catheter as recited in claim 1 within a vessel to the vicinity of the target cells;
   isolating an intravascular space containing the lesion by inflating proximal and distal balloons attached to the catheter; and
   withdrawing blood from space isolated by said balloons through a suction port of the catheter and injecting gas into the isolated space through a gas injection port of the catheter;
   bombarding the arterial wall containing the target cells with DNA-coated particles so as to deliver genetic material thereto using an operating head attached to said catheter wherein said operating head contains a particle bombardment device disposed therein for discharging particles coated with DNA through a discharge port of said operating head so that particles impinge in vivo on target tissue and deliver the DNA intracellularly thereto and further wherein said operating head includes telescoping sections such that said discharge port is sealed when covered by one of the telescoping sections; and
   operating an hydraulic cylinder within said operating head for moving one of said telescoping sections with respect to the other so as to seal and unseal said discharge port.

7. A method in accordance with claim 6 wherein the method is performed subsequent to a percutaneous transluminal angioplasty procedure.

8. A catheter for transferring medical material in vivo to a target tissue comprising:
   an elongated hollow flexible tubular member adapted to be inserted within a blood vessel; and an operating head attached to said tubular member and containing a particle bombardment device disposed therein for discharging particles coated with medical material so that particles impinge in vivo on target tissue and deliver the medical material intracellularly thereto;

a discharge port disposed on said operating head through which are discharged said particles;

wherein said operating head comprises a hydraulic cylinder and piston within said operating head and telescoping proximal and distal sections which act to seal and unseal said discharge port in accordance with the operation of said hydraulic cylinder and piston;

means for isolating a space within the vessel containing the operating head and removing fluid therefrom;

means for sealing said discharge port from body fluids until the fluid is removed from the space isolated by said isolating means.

9. A catheter in accordance with claim 8 wherein said isolating means comprises proximal and distal balloons girthing said tubular member supported adjacent said operating head and further comprising:

a balloon inflation line running through said tubular member and communicating with said proximal and distal balloons so as to provide inflation pressure thereto; and wherein inflation of said proximal and distal balloons against the walls of an artery or other body duct in which said catheter is inserted serves to isolate a space therebetween into which coated particles may be discharged from said operating head toward a target tissue.

10. A catheter in accordance with claim 9 further comprising suction and gas injection lines and respective ports communicating with said suction and gas injection lines running through said tubular member which enable body fluids in the space isolated by said proximal and distal balloons to be displaced by gas.

11. A catheter in accordance with claim 8 wherein said particle bombardment device comprises:

a pair of electrodes for vaporizing a liquid droplet in a discharge chamber so as to create a shock wave therein;

a carrier sheet suspended within said discharge chamber and onto which are precipitated coated gold particles; and a mesh screen within said discharge port for retaining said carrier sheet when the latter is propelled thereagainst by a shock wave while allowing the accelerated coated particles to proceed to the target tissue.

12. A catheter in accordance with claim 9 further comprising medical material and wherein the medical material is DNA.

13. A gene therapy instrument comprising:

an elongated hollow tubular member adapted to be inserted within a body cavity;

an operating head attached to said tubular member and containing a particle bombardment device disposed therein for discharging DNA-coated particles so that the particles impinge on a target tissue and deliver DNA intracellularly thereto;

a discharge port on said operating head out through which are discharged said particles;

a gas discharge port for insufflating a region within a body cavity into which said operating head is inserted to displace fluid therefrom and provide a medium into which said particles may travel;

a first fiber optic light pipe within said tubular member for transmitting light from said operating head to illuminate the region in which said operating head is located; and, a second fiber optic light pipe within said tubular member for receiving and transmitting visual image information of the illuminated region so as to enable said operating head to be guided to the target tissue.

14. A gene therapy instrument in accordance with claim 13 wherein said particle bombardment device comprises:

a pair of electrodes for vaporizing a water droplet in a discharge chamber so as to create a shock wave therein;

a carrier sheet suspended within said discharge chamber and onto which are precipitated DNA-coated gold particles; and a mesh screen within said discharge port for retaining said carrier sheet when the latter is propelled thereagainst by a shock wave while allowing the accelerated DNA-coated particles to proceed to the target tissue.

15. A gene therapy instrument in accordance with claim 13 wherein said operating head comprises telescoping sections relatively movable such that said discharge port is sealed when covered by one of the telescoping sections.

16. A gene therapy instrument in accordance with claim 15 further comprising a fluid pressure operated actuator within said operating head for moving one of said telescoping sections with respect to the other so as to seal and unseal said discharge port.

17. A gene therapy instrument in accordance with claim 13 further comprising:

proximal and distal balloons girthing said tubular member and supported adjacent said operating head; and a balloon inflation line running through said tubular member and communicating with said proximal and distal balloons so as to provide inflation pressure thereto.

* * * * *